United States Patent
Streng et al.

(10) Patent No.: US 6,931,276 B2
(45) Date of Patent: Aug. 16, 2005

(54) METHOD AND DEVICE FOR USE IN MICTURITION STUDIES

(76) Inventors: Tomi Streng, Ahdetie 41, FIN-20460, Turku (FI); Antti Talo, Koivuharjunkatu 25, FIN-20600, Littoinen (FI); Risto Santti, Mannerheiminkatu 23, FIN-21100, Naantali (FI)

( * ) Notice: Subject to any disclaimer, the term of this patent is extended or adjusted under 35 U.S.C. 154(b) by 353 days.

(21) Appl. No.: 10/133,369

(22) Filed: Apr. 29, 2002

(65) Prior Publication Data

US 2003/0204149 A1 Oct. 30, 2003

(51) Int. Cl.⁷ .............................................. A61B 5/04
(52) U.S. Cl. ....................................... 600/546; 600/547
(58) Field of Search ................................. 600/547, 546

(56) References Cited

U.S. PATENT DOCUMENTS

| | | | |
|---|---|---|---|
| 4,063,548 A | 12/1977 | Klatt et al. | 128/2 R |
| 5,972,921 A | 10/1999 | Santti et al. | 514/177 |
| 6,434,418 B1 | 8/2002 | Neal et al. | 600/511 |
| 6,666,828 B2 * | 12/2003 | Greco et al. | 600/561 |
| 2003/0100930 A1 * | 5/2003 | Cohen et al. | 607/40 |

FOREIGN PATENT DOCUMENTS

| | | | |
|---|---|---|---|
| DE | 195 05 632 | 8/1996 | |
| EP | 0 608 593 | 8/1994 | |
| GB | 2145932 | 4/1985 | |
| WO | WO 94/15667 | 7/1994 | |
| WO | WO 97/46972 | 12/1997 | |
| WO | WO 99/18851 * | 4/1999 | ......... A61B/5/0488 |

* cited by examiner

*Primary Examiner*—Eric F. Winakur
*Assistant Examiner*—Matthew J Kremer
(74) *Attorney, Agent, or Firm*—James C. Lydon

(57) ABSTRACT

Method and device for the sensing of the electromyographic activity of an individual's bladder detrusor muscle, where an elongated electrode is inserted through the individual's urethra, so that the proximal end of the electrode becomes positioned in the bladder, and the bladder is charged with a fluid having electrical conductivity, and the electrical potential of the detrusor muscle, mediated by the fluid, is sensed by the electrode.

19 Claims, 5 Drawing Sheets

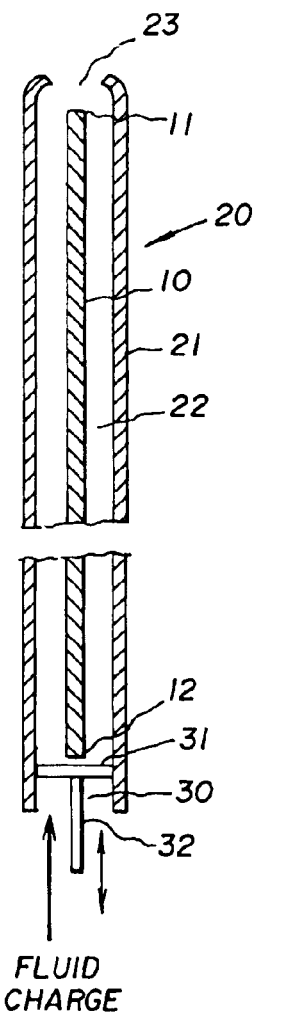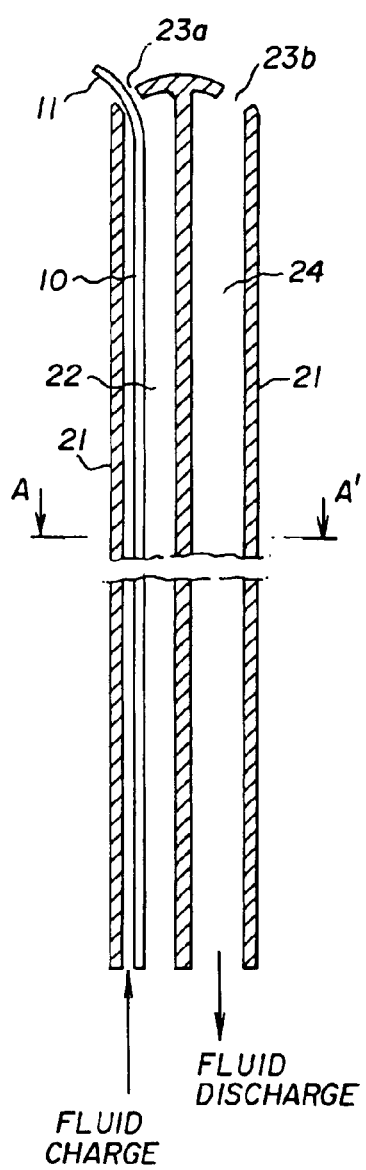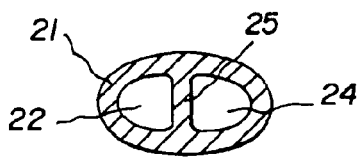

METHOD AND DEVICE FOR USE IN MICTURITION STUDIES

FIELD OF THE INVENTION

This invention relates to novel methods and devices for use in micturition studies, especially to a non-invasive method and device for sensing of electromyographic activity of the detrusor muscle, preferably in combination with bladder pressure and flow rate recordings.

BACKGROUND OF THE INVENTION

The publications and other materials used herein to illuminate the background of the invention, and in particular, cases to provide additional details respecting the practice, are incorporated by reference.

The micturition reflex is comprised of a plurality of interrelated neurological reflexes involved in urination. The function of the lower urinary tract includes maintenance of urinary continence and periodic expulsion of urine during voiding. The latter functions involve sympathetic, parasympathetic and somatic nerves. Continence is maintainable by urethral sphincter muscles, which preferably controllably contract the bladder urethra, acting as a valve. Discharge of urine is facilitated by sphincter relaxation. Urinary sphincters may also have an auxiliary function in maintenance of flow rate. Micturation also requires coordinated operation of the detrusor muscle, which locates inside the bladder wall. Impairment of one or more of the neurological reflexes associated with proper sphincter or detrusor action can result in inefficient or impaired bladder operation.

Cystometry is a diagnostic procedure for evaluating bladder function whereby an accurate picture of normal and abnormal micturition physiology is derived. Cystometric evaluation of micturition disturbances permits an orderly system of classification of neurogenic bladders. The procedure involves distension of the bladder by filling it with a gas or liquid through an inserted catheter. As fluid is inserted interiorly of the bladder, the relation between intravesical bladder pressure and inputted volume of fluid is graphically determined.

Sphincter electromyography is a diagnostic technique in which micturition electrical responses of the urinary sphincters are graphically displayed. Electromyography has been used in detecting lesions of the lower motor neurons and peripheral nerves and in diagnosing primary skeletal muscle disease. The sphincter response is sensed by utilization of externally contacting electrodes. Usually, electronic amplifying apparatus is provided to process the sphincter signals sensed by the electrodes such that the signal may be displayed; for example, on a strip chart recorder. The electromyogram (EMG) produced by the technique provides a useful graphical monitor of sphincter electrical activity, particularly where a patient is unable to control voiding.

U.S. Pat. No. 4,063,548 (Klatt et al.) describes a device for simultaneous cystometry and electromyography. The apparatus comprises a gas cystometry system for monitoring bladder detrusor reflexes and an electromyographic monitoring system which can be combined within a unitary enclosure. The cystometry system comprises a catheter for injecting fluid interiorly of the bladder and associated electronic circuitry for deriving interior bladder pressure. The electromyographic system comprises one or more electrodes for sensing sphincter electrical activity and electronic circuitry interconnected with the electrodes for amplifying sphincter electrical outputs. The electromyographic electrodes are operably mounted at the bladder-engaging end of a cystometric catheter. The device according to this publication does not, however, provide any facilities for sensing detrusor electrical activity.

U.S. Pat. No. 5,972,921 (Santti et al.) relates to a method for the treatment of detrusor urethral sphincter dyssynergia in men. The publication describes also a method for in vivo investigation of the urinary function based on an animal model of rats. The rats are anesthetized, provided with a pressure transducer connected to an infusion cannula inserted in the bladder, a flow probe inserted in the distal urethra and connected to a flow meter. The animals are infused with a solution into the bladder to induce micturition. The bladder pressure and urinary flow are registered as function of time. The rats are further provided with suction electrodes attached to the detrusor muscle, bladder neck and the external urethral sphincter (EUS, also called rhabdosphincter). The electrical activity of these muscles is thus registered simultaneously with the registering of the bladder pressure and the urinary flow.

The investigation method and device described in the cited patent would not be practical for routine diagnostic use on humans. The application of the suction electrodes on the muscles and the insertion of the infusion cannula through the bladder are invasive measures which would require anaesthesia of the patient and the assistance of a doctor.

So far, no publications have been found relating to non-invasive sensing of electrical activity of the detrusor muscle, with or without simultaneous recording of bladder pressure (transvesical cystometry) and flow rate. Simultaneous non-invasive sensing of detrusor muscle and external urethral sphincter electrical activities, optionally combined with sensing of bladder pressure, has not either been found in the art.

OBJECTS AND SUMMARY OF THE INVENTION

One object of this invention is to provide a non-invasive method and device for sensing of electromyographic activity of the detrusor muscle.

Another object is to provide a method and device for simultaneous, non-invasive sensing of electromyographic activities of the detrusor muscle as well as the external urethral sphincter.

A third object is to provide a method and device for simultaneous, non-invasive sensing of electromyographic activity of the detrusor muscle and bladder pressure.

A fourth object is to provide a method and device for simultaneous sensing of electromyographic activities of the detrusor muscle and the external urethral sphincter as well as the bladder pressure, wherein all parameters are sensed in a non-invasive manner.

Thus, according to the broadest aspect, this invention concerns a method for sensing of the electromyographic activity of an individual's bladder detrusor muscle, wherein
an elongated electrode is inserted through the individual's urethra, so that the proximal end of the electrode becomes positioned in the bladder, and
the bladder is charged with a fluid having electrical conductivity, and
the electrical activity of the detrusor muscle, mediated by the fluid, is sensed by the electrode.

The device according to this invention is in its broadest aspect defined as a device for recording of the electromyographic activity of an individual's bladder detrusor muscle, wherein said device is intended to be inserted through the individual's urethra. Said device comprises an elongated electrode having a proximal end adapted to receive the bladder, and a distal end. The device comprises further means for recording and the electrical potential sensed by the electrode.

BRIEF DESCRIPTION OF THE DRAWINGS

FIG. 2 shows a longitudinal section of the device according to one embodiment.

FIG. 3 shows a longitudinal section of the device according to a second embodiment.

FIG. 4 is a lateral cross section of FIG. 3, taken on line A–A'.

FIG. 5 is a longitudinal view of the device according to a further embodiment.

DETAILED DESCRIPTION OF THE INVENTION

In the following, the term "proximal" shall mean the end of the device to be directed inwards to the bladder, and the term "distal" shall mean the opposite end of the device.

Figure 1:
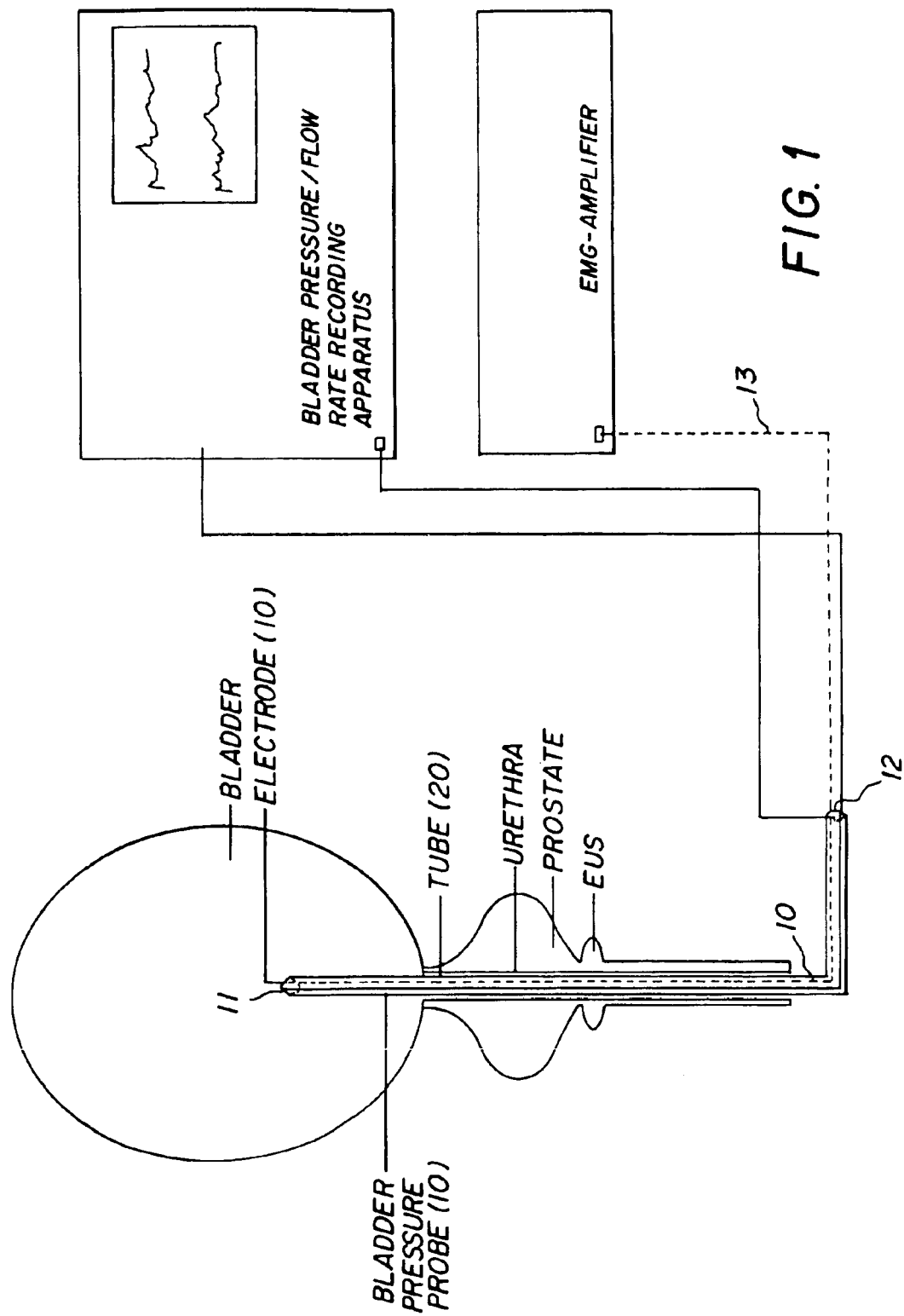
FIG. 1 is a schematic overview of the device according to one embodiment of the invention, inserted in the urethra and bladder and connected to recording apparatuses.

In FIG. 1, a schematic overview of the device according to one embodiment of the invention is shown. An elongated threadlike electrode 10, surrounded by a protective tube 20, is inserted in a male patient's urethra so that the proximal end 11 of the electrode is positioned in the patient's bladder. The bladder is charged with an electrically conductive fluid, such as an aqueous electrolyte solution, preferably a physiological saline solution, through the channel of the tube 20. The detrusor reflex is evoked by the bladder filling, and the electrode 10 senses the electrical activity of the detrusor muscle, mediated by the electrically conductive fluid. The distal end 12 of the electrode is connected to a wire 13 which in turn is connected to a means for recording and displaying the sensed signal, including the necessary electronic components, such as amplifiers, converters, a computer and a display. On the outer side of the tube is arranged a probe 40 for sensing the bladder pressure. This probe is connected to a means for recording and displaying the sensed pressure signal. The flow rate of the charged fluid is also recorded and displayed.

FIG. 2 shows a longitudinal section of the device according to one embodiment. The threadlike electrode 10 is surrounded by the protective tube 20 so that also the proximal end 11 of the electrode is positioned inside the tube. It is preferable to have the proximal end 11 positioned within the tube during the insertion step in order to avoid damages on the urethral wall and/or the electrode. The wall of the tube is denoted 21 and the channel 22. The proximal end of the tube is provided with an opening 23. When the device is properly inserted so that the proximal end is situated in the bladder, the proximal end 11 of the electrode is released from the protective tube, to come in good contact with the fluid in the bladder (see FIG. 1). This release can be performed in various ways. According to the embodiment shown in this figure, the device comprises a plunger 30, having a head 31 and a shaft 32. The plunger is arranged to be longitudinally movable (as shown by the arrows) in the protective tube 20. The proximal end 31 (or head) of the plunger is construed to act on the electrode 10, for example on the distal end 12 of the electrode as shown in the figure, or, for example, on a protrusion or the like arranged on the middle part of the electrode (not shown in the figure). Because a free passage in the channel 22 for the charge of the conductive fluid must be ensured, the head of the plunger shall be perforated, for example construed as a grid of electrically non-conductive threads. When the device is inserted in its desired position, the plunger, and subsequently the electrode, can be pushed forwards (in the proximal direction) so as to enforce the end 11 of the electrode to protrude the opening 23. Alternatively, the plunger and electrode being kept in a fixed position, the tube 20 can be drawn backwards (in the distal direction) so as to release the end 11 of the electrode.

FIGS. 3 and 4 show another embodiment of the device according to this invention. In this alternative, the tube 20 has two parallel channels 22 and 24, separated by the wall 25. The proximal end of the tube has two openings, 23 a for the channel 22 and 23 b for the channel 24. The electrode 10 is situated in the channel 22. The channel 22 is used for the charge and the channel 24 for the discharge of the fluid.

A further embodiment of the invention is shown in FIG. 5, which is a side view of the tube 20 with the electrode 10 positioned therein. A probe 40 for sensing the bladder pressure is arranged on the outer side of the tube 20. The tubing may be a tubing commonly used in clinical practice, namely a double or triple lumen cystometry catheter. The electrode is preferably inserted via the catheter lumen through which the bladder is charged with fluid. Alternatively, or in addition, at least one ring-shaped electrode 41, intended for sensing the electromyographic activity of the urethral sphincter, is arranged on the outer side of the tube 20. The electrode 41 is arranged at a position so as to come in contact with the external urethral sphincter when the tube 20 is properly inserted. The bladder pressure probe 40 is located on the tube 20 at a position so as to become positioned inside the bladder.

The tubing may be a double or triple lumen cystometry catheter generally used in clinical practice. The wire electrode is introduced via the catheter lumen through which the bladder is filled with fluid.

The device can further comprise means for recording the bladder pressure sensed by the pressure probe 40 and/or means for recording the electromyographic activity of the urethral sphincter, sensed by the electrode 41. Such means comprise the necessary electronic components, optionally including a computer, for recording and displaying the sensed parameters.

The electrode 10 is made of a suitable electrically conductive material, such as a metal or metal alloy. Particularly preferable materials are silver or platinium with teflon coating, which insulates the electrode leaving only the tip 11 of the electrode without coating. The tip of the electrode is thus allowed to sense the electrical potential.

As the electrode can be a threadlike body, its distal end 12 can according to one alternative be directly connected to the recording unit. Alternatively, the distal end 12 can be connected to a separate wire 13, which in turn is connected to the recording unit (as shown in FIG. 1).

FIGS. 1, 3 and 5 show the alternative where the proximal end 11 of the electrode is located outside the tube during recording. This arrangement is, however, not necessary. According to another alternative, the proximal end may be positioned inside the tube (as in FIG. 2) during sensing of EMG of the detrusor muscle, particularly in case the electrode 10 is located in the lumen 22 through which the electrically conductive fluid is charged (see e.g. FIG. 3).

The electrically conductive fluid to be charged into the bladder is preferably an aqueous electrolyte solution, most preferably a physiological saline solution.

Figure 6:
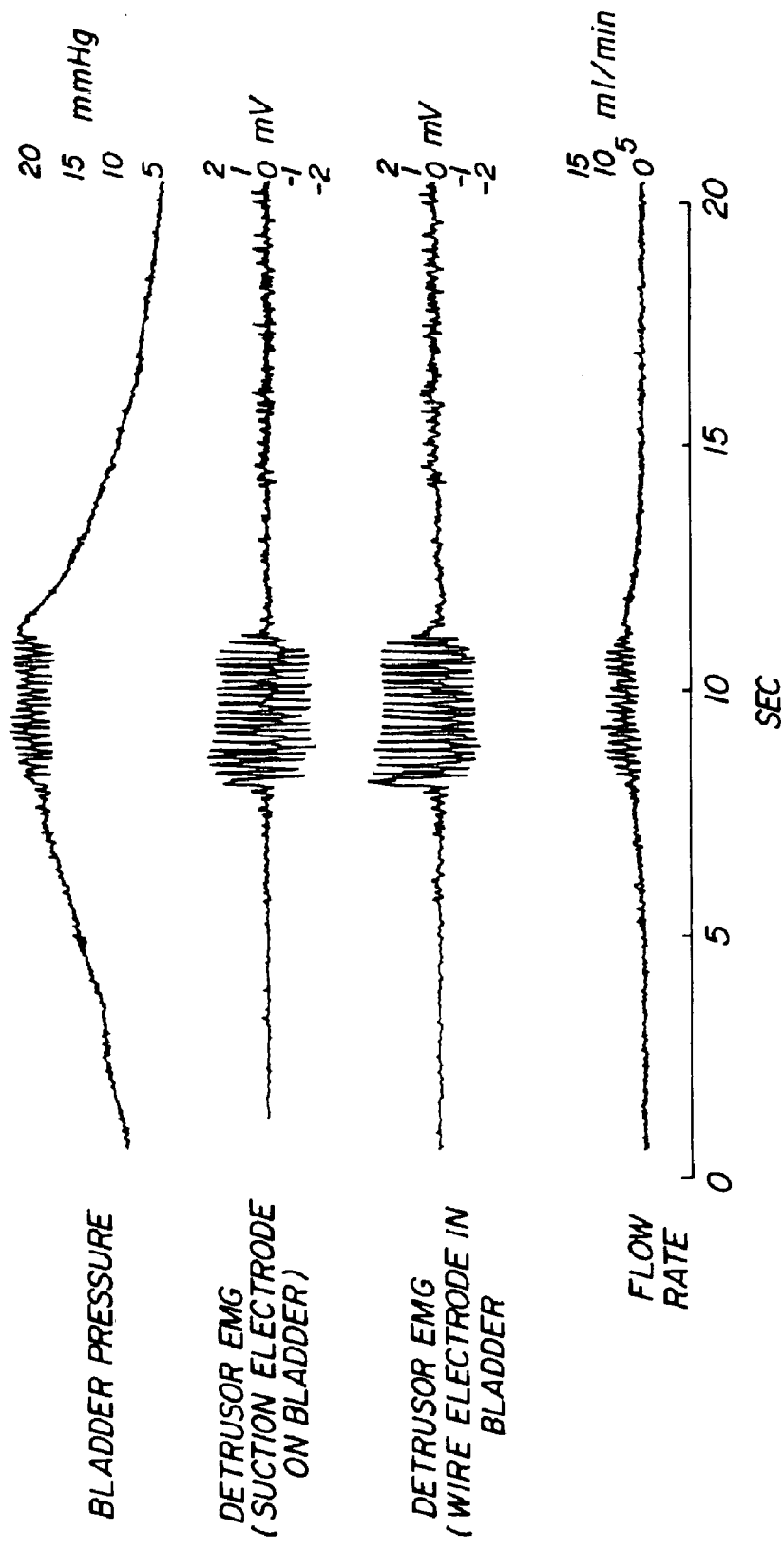
FIGS. 6 to 8 show simultaneous recordings of bladder pressure, flow rate and detrusor EMG, measured with the electrode according to the invention and with a conventional suction electrode in an animal experiment.
Figure 7:
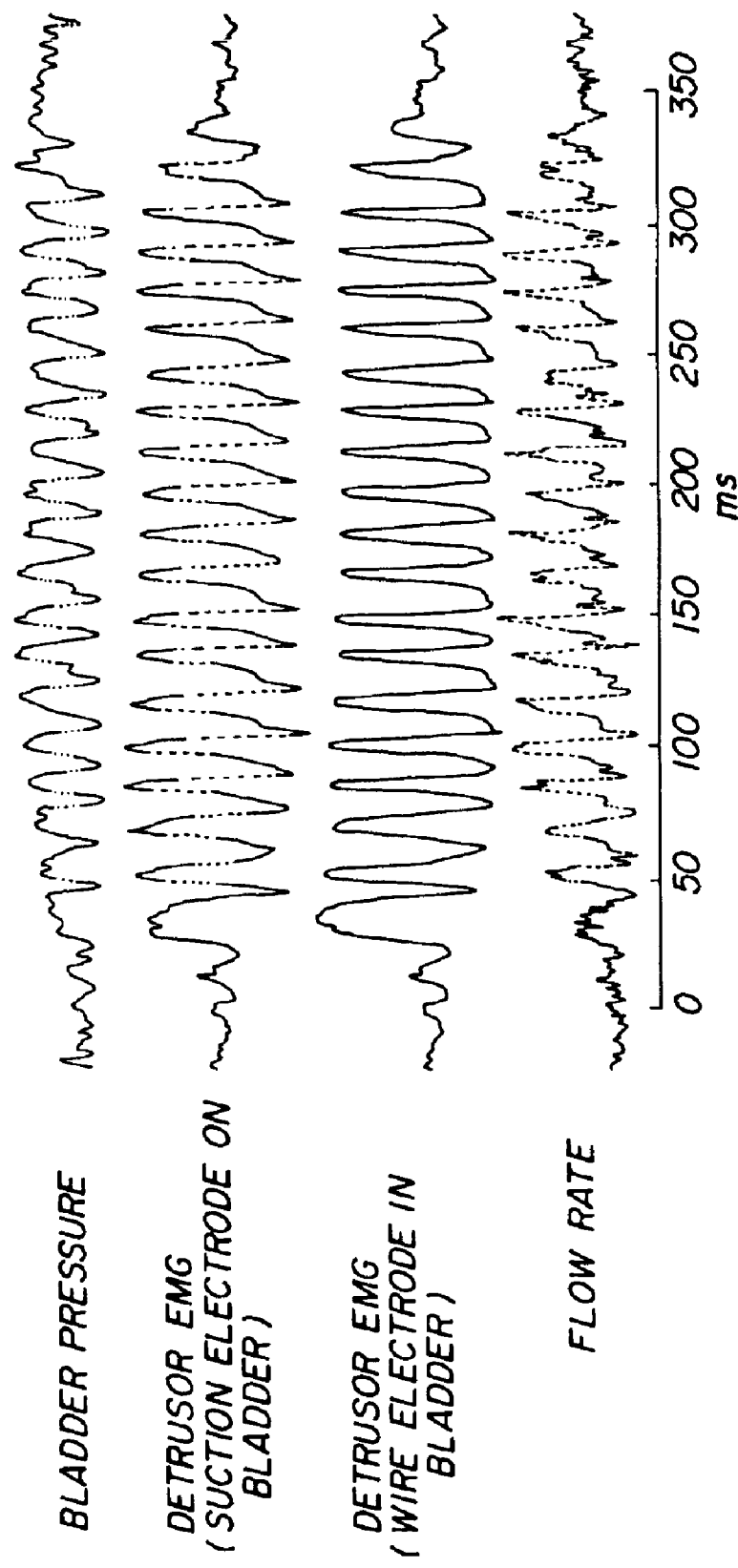
Figure 8:
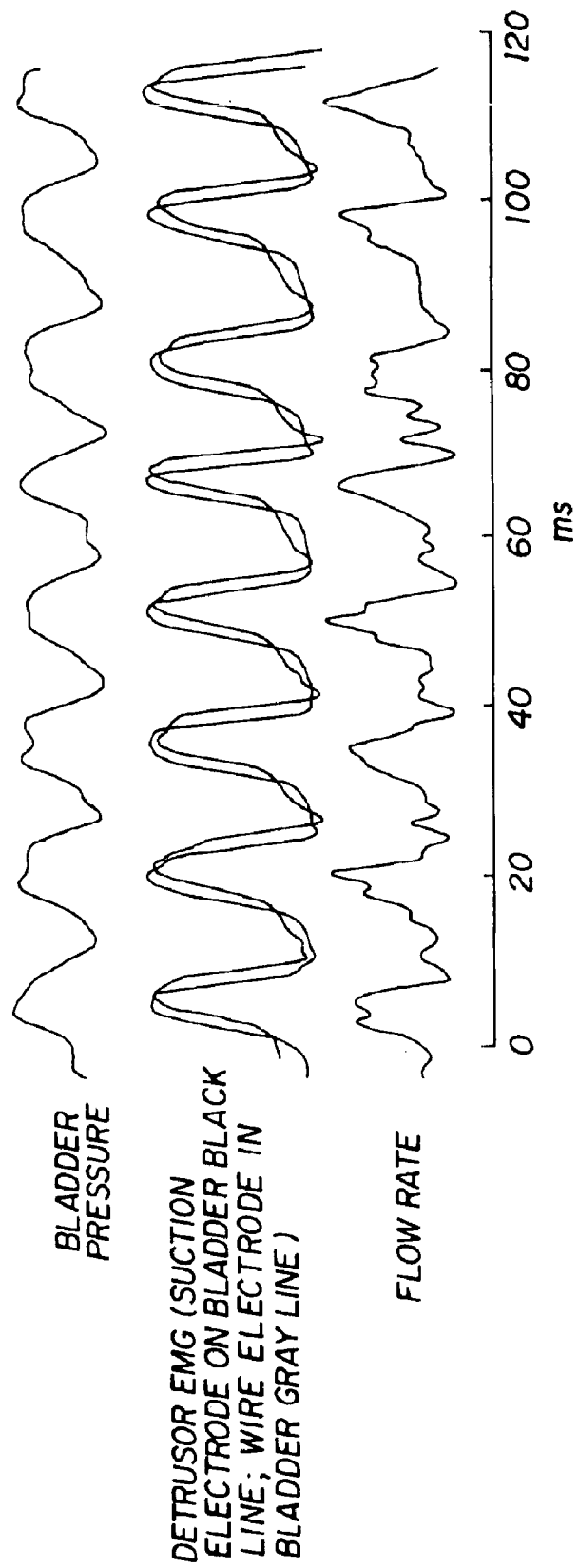

FIGS. 6 to 8 show simultaneous recordings of bladder pressure, flow rate and detrusor EMG, measured with the electrode according to the invention and also with a conventional suction electrode in a micturation experiment with an adult male Noble rat.

As can be seen from FIG. 6, the electrical activity of the detrusor muscle was recorded with two different electrodes: a conventional suction electrode, which records the extracellular activity from the bladder surface, and with a wire electrode according to this invention, wherein the wire electrode was positioned inside the bladder as described above. The electrical activity was conducted from the detrusor muscle through the saline in the bladder. The flow rate recording is also shown during a typical micturation contraction of the Noble rat used in the experiment. FIG. 7 shows an extended recording of bladder pressure, detrusor EMG and flow rate recordings. In FIG. 8, the detrusor EMG recordings for the two electrodes are superimposed, showing highly similar activity.

The invention described above provides many advantageous features over prior art: 1) it is the sole non-invasive method and device for studying the electrical activity of the detrusor muscle ever disclosed, and 2) non-invasive cystometry, including bladder pressure sensing and measuring of flow rate, which are used in common clinical practice, can easily be combined with non-invasive electromyography sensing of the detrusor and rhabdosphincter muscles. Therefore, this device, which could be used by a nurse, offers a possiblity for easy routine diagnostics of patients suffering from neuronal micturition problems, such as overactive bladder and functional disorder of the lower urinary tract, both male and female patients.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

What is claimed is:

1. Method for the sensing of the electromyographic activity of an individual's bladder detrusor muscle, wherein
   an elongated electrode is inserted through the individual's urethra, so that the proximal end of the electrode becomes positioned in the bladder, and
   the bladder is charged with a fluid having electrical conductivity, and
   the electrical potential of the detrusor muscle, mediated by the fluid, is sensed by the electrode.

2. The method according to claim 1, wherein the electrode is inserted by use of a protective tube.

3. The method according to claim 2, wherein the proximal end of the electrode is protected by the protective tube during the insertion step, and said proximal end is released from the protective tube when located in the desired position.

4. The method according to claim 2, wherein the bladder is charged with the fluid through the channel of the protective tube.

5. The method according to claim 4, wherein the fluid is charged by use of a protective tube having an additional channel for the discharge.

6. A method according to claim 2, wherein the bladder pressure is sensed simultaneously by a pressure probe, located on the protective tube at a position so as to become positioned inside the bladder.

7. A method according to claim 2, wherein the electromyographic activity of the urethral sphincter is sensed simultaneously by one or more electrodes arranged on the outer side of the protective tube at a position so as to come in contact with the external urethral sphincter when the protective tube is properly inserted.

8. The method according to claim 7, wherein the bladder pressure is sensed simultaneously by a pressure probe located on the protective tube at a position so as to become positioned inside the bladder.

9. The method according to claim 1, wherein the fluid is an aqueous electrolyte solution.

10. A device for the recording of the electromyographic activity of an individual's bladder detrusor muscle, wherein said device is intended to be inserted through the individual's urethra, said device comprising
    an elongated electrode adapted to sense electromyographic activity of the detrusor muscle, said electromyographic activity being mediated by an electrically conductive fluid in the bladder, said electrode being an elongated threadlike body made of a metal or metal alloy, the proximal end of said electrode being adapted to to be received in the bladder, and
    a distal end, and
    means for recording the electrical activity sensed by the electrode.

11. The device according to claim 10, comprising a protective tube surrounding the electrode.

12. The device according to claim 11, comprising a plunger, arranged to be longitudinally movable in the protective tube, said plunger having a proximal end adapted to receive the electrode.

13. The device according to claim 11, wherein the protective tube has at least two parallel channels.

14. The device according to claim 11, wherein a pressure probe, intended for sensing the bladder pressure, is arranged on the outer side of the protective tube.

15. The device according to claim 14, comprising means for recording the bladder pressure sensed by the pressure probe.

16. The device according to claim 11, wherein at least one electrode, intended for sensing the electromyographic activity of the urethral sphincter, is arranged on the outer side of the protective tube.

17. The device according to claim 16, wherein a pressure probe, intended for sensing the bladder pressure, is arranged on the outer side of the protective tube.

18. The device according to claim 17, comprising means for recording the bladder pressure sensed by the pressure probe and means for recording the electromyographic activity of the urethral sphincter, sensed by the electrode.

19. The device according to claim 16, comprising means for recording the electromyographic activity of the urethral sphincter, sensed by the electrode.

* * * * *